United States Patent
Voegel et al.

(10) Patent No.: US 8,795,705 B2
(45) Date of Patent: *Aug. 5, 2014

(54) DERMATOLOGIC COMPOSITIONS COMPRISING PYRROLIDONE-5-CARBOXYLIC ACID AND AT LEAST ONE ENTITY CHOSEN FROM CITRULLINE, ARGININE AND ASPARAGINE, AND USES THEREOF IN THE TREATMENT OF ATOPIC DERMATITIS

(75) Inventors: Johannes Voegel, Chateauneuf/Grasse (FR); Emmanuelle At, Antibes (FR); Carine Rosignoli, Biot (FR)

(73) Assignee: Galderma Research & Development, Biot (FR)

( * ) Notice: Subject to any disclaimer, the term of this patent is extended or adjusted under 35 U.S.C. 154(b) by 451 days.

This patent is subject to a terminal disclaimer.

(21) Appl. No.: 12/601,113

(22) PCT Filed: May 22, 2008

(86) PCT No.: PCT/EP2008/056333
§ 371 (c)(1),
(2), (4) Date: Aug. 9, 2010

(87) PCT Pub. No.: WO2008/142147
PCT Pub. Date: Nov. 27, 2008

(65) Prior Publication Data
US 2010/0291002 A1 Nov. 18, 2010

Related U.S. Application Data

(60) Provisional application No. 60/924,712, filed on May 29, 2007.

(30) Foreign Application Priority Data

May 22, 2007 (FR) .................................... 07 55186

(51) Int. Cl.
*A61F 2/00* (2006.01)

(52) U.S. Cl.
USPC ........................................................ 424/423

(58) Field of Classification Search
None
See application file for complete search history.

(56) References Cited

U.S. PATENT DOCUMENTS

| 4,837,019 A * | 6/1989 | Georgalas et al. .............. 424/59 |
| 2006/0063827 A1 | 3/2006 | Yu et al. |

FOREIGN PATENT DOCUMENTS

| DE | 43 41 000 A1 | 6/1995 |
| DE | 103 93 402 T5 | 9/2005 |

(Continued)

OTHER PUBLICATIONS

SpecialChem, Ajidew A-100, Last Accessed Jul. 31, 2012, SpecialChem4Cosmetics, 1 page, http://www.specialchem4cosmetics.com/tds/ajidew-a-100/ajinomoto/884/index.aspx.*

(Continued)

*Primary Examiner* — Trevor Love
(74) *Attorney, Agent, or Firm* — Finnegan, Henderson, Farabow, Garrett & Dunner LLP

(57) ABSTRACT

Combination comprising pyrrolidone-5-carboxylic acid and at least one compound from citrulline, arginine and asparagine, and use thereof in the treatment of atopic dermatitis The present invention relates to a composition comprising, in a physiologically acceptable carrier, pyrrolidone-5-carboxylic acid and at least one compound from citrulline, arginine and asparagine, in racemic or isomer form, and salts thereof, for the preparation of a medicament for use in the treatment and/or prevention of atopic dermatitis.

17 Claims, 6 Drawing Sheets

(56) References Cited

FOREIGN PATENT DOCUMENTS

Figure 1:
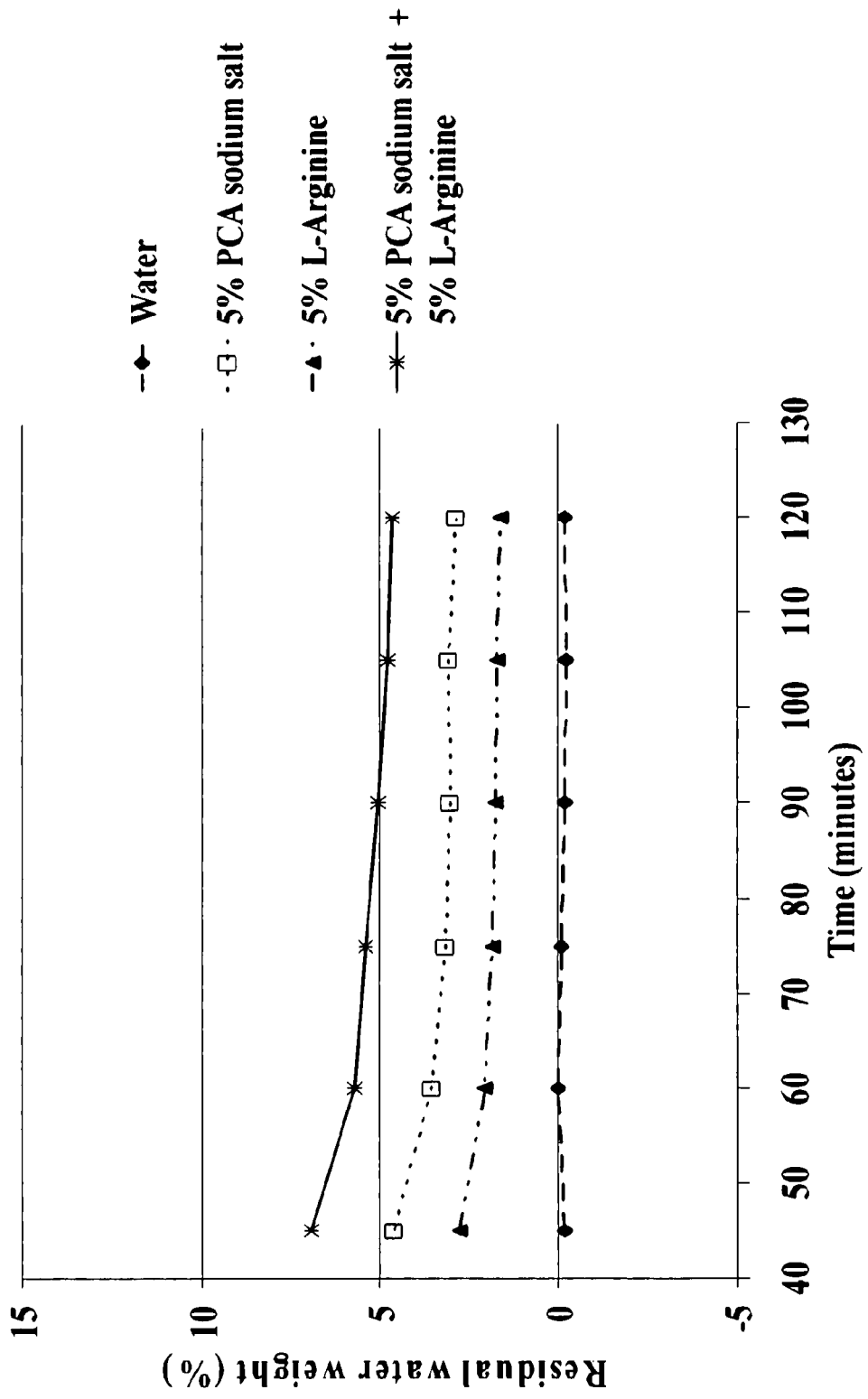

EP 1 226 822 A2 7/2002
JP 9-87126 3/1997

OTHER PUBLICATIONS

International Search Report for PCT/EP2008/056333, dated Oct. 1, 2008, 3 pages.

English language abstract of DE 43 41 000 A1, Jun. 8, 1995, 5 pages.
English language abstract of DE 103 93 402 T5, Sep. 29, 2005, 4 pages.
English language abstract of JP 9-87126, Mar. 31, 1997, 3 pages.
Chamlin, S. et al., "Ceramide-dominant barrier repair lipids alleviate childhood atopic dermatitis: Change in barrier function provided a sensitive indicator of disease activity," American Academy of Dermatology, Inc. 47(2): 198-208 (Aug. 2002).

* cited by examiner

DERMATOLOGIC COMPOSITIONS COMPRISING PYRROLIDONE-5-CARBOXYLIC ACID AND AT LEAST ONE ENTITY CHOSEN FROM CITRULLINE, ARGININE AND ASPARAGINE, AND USES THEREOF IN THE TREATMENT OF ATOPIC DERMATITIS

CROSS REFERENCE TO RELATED APPLICATIONS

This application is a National Phase application based on PCT/EP2008/056333 filed on May 22, 2008, and claims the priority of French Application No. 0755186, filed on May 22, 2007, and the benefit of U.S. Provisional Application No. 60/924,712, filed on May 29, 2007, the content of all of which is incorporated herein by reference.

The present invention relates to combinations which are particularly suitable for the treatment and/or prevention of atopic dermatitis.

Atopic dermatitis, also called eczema, is a condition of the epidermis which affects a large number of individuals, including children and adolescents. In Europe, approximately 10% of children and 20% of the population are affected, with an increase in the number of cases over the last few decades.

Atopic dermatitis occurs in individuals genetically predisposed to atopy and the manifestations of atopy, namely asthma, allergic rhinitis and allergies. This chronic skin disease, which is inflammatory in nature, is due to complex interactions between the genetic predispositions of the individual and environmental factors. Many genetic studies have focused on the immunological mechanisms.

Atopic dermatitis is a common condition in individuals of both sexes, often from the age of three months, which is characterized by repeating outbreaks of eczema on skin characterized by dry, squamous and highly pruriginous lesions. It has been noted that dryness of the skin is one of the predominant factors in the generation of atopic dermatitis. Recently, the influence of a deficiency of the epithelial barrier has been studied. In particular, Palmer et al. (Common loss-of-function variants of the epidermal barrier protein filaggrin are a major predisposing factor for atopic dermatitis. Nat. Genet. 2006 Apr; 38(4):441-6) and Weidinger et al. (Loss-of-function variations within the filaggrin gene predispose for atopic dermatitis with allergic sensitizations. J Allergy Clin Immunol. 2006 Jul; 118(1):214-9.) report that certain variants of the gene encoding filaggrin, an epithelial barrier protein, are predisposing factors for atopic dermatitis. Moreover, Seguchi et al. and Jensen et al. have demonstrated a reduced expression of filaggrin in the skin of individuals affected by atopic dermatitis (Jensen J M. et al., Impaired sphingomyelinase activity and epidermal differentiation in atopic dermatitis. J Invest Dermatol. 2004 Jun; 122(6):1423-31; Seguchi T. et al., Decreased expression of filaggrin in atopic skin. Arch Dermatol Res. 1996 Jul; 288(8):442-6).

Following its structural function, filaggrin is broken down in the stratum corneum so as to release the pool of free amino acids which plays an important role in hydrating the skin. The observations by Palmer et al. and by Weidinger et al. should therefore be looked at in relation to the decreased hydration of the stratum corneum in atopic dermatitis, as has been observed by Tagami et al. (Decreased hydration state of the stratum corneum and reduced amino acid content of the skin surface in patients with seasonal allergic rhinitis. Br J. Dermatol. 1998 Oct; 139(4):618-21).

In addition to the twenty natural amino acids which are incorporated into filaggrin at the time of the translation step, it should be noted that all three of citrulline, urocanic acid and pyrrolidone-5-carboxylic acid, which are products corresponding to amino acid derivatives, are also present in filaggrin hydrolysates. When filaggrin is broken down, these three compounds are released together with the amino acids in the form of monomers and constitute important components of the "free amino acid" pool found in the stratum corneum (Scott I R, Harding C R, Barrett J G. Histidine-rich protein of the keratohyalin granules. Source of the free amino acids, urocanic acid and pyrrolidone carboxylic acid in the stratum corneum. Biochim Biophys Acta. 1982 Oct. 28; 719(1):110-7; Horii I et al. Histidine-rich protein as a possible origin of free amino acids of stratum corneum. J. Dermatol. 1983 Feb; 10(1):25-33; Scott I R, Harding C R. Filaggrin breakdown to water binding compounds during development of the rat stratum corneum is controlled by the water activity of the environment. Dev Biol. 1986 May; 115(1):84-92).

Several publications propose the use of pyrrolidone carboxylic acid as a moisturizing agent in emollient compositions for treating atopic dermatitis (Takaoka, JP2004168763; Fukiya, JP2002053428; Nakamura and Takada, JP61215307, JP61215308 and JP62267215). Harano et al., in patent application WO2005077349, for their part, propose, among other components, the use of citrulline or of certain amino acids (glycine, methionine, alanine) for treating atopic dermatitis. Nenoff et al. (Topically applied arginine hydrochloride. Effect on urea content of stratum corneum and skin hydration in atopic eczema and skin aging; Hautarzt 2004 Jan; 55(1): 58-64) describe the use of arginine hydrochloride in atopic dermatitis with the aim of reconstituting the urea deficiency which is observed in this pathological condition. They note an improvement in the symptoms of dry skin. Moreover, with the aim of improving atopic dermatitis, Tezuka and Tezuka (JP08020525) have proposed shampoos containing a complex of sodium montmorillonite with a moisturizing agent, which itself can be urea, amino acids, proteins, pyrrolidone carboxylic acid or a silk protein hydrolysate.

In this context where there exists a need for new treatments for atopic dermatitis, the inventors provide novel solutions by proposing combinations of compounds, more particularly pharmaceutical or dermatological compositions which make it possible to compensate for, to a greater extent, the epithelial barrier deficiency.

In fact, the application of a combination or composition containing pyrrolidone-5-carboxylic acid and at least one compound from citrulline, arginine and asparagine, in racemic or isomer form, and also salts thereof, has a moisturizing action on this part of the skin, thereby leading to a significant effect for the treatment of atopic dermatitis.

The combinations or compositions according to the invention are particularly suitable for the treatment of atopic dermatitis or eczema, both in adults and in children.

A subject of the present invention is therefore a combination of pyrrolidone-5-carboxylic acid with at least one of the compounds chosen from citrulline, arginine and asparagine, in racemic form or in D- or L-isomer form, and/or salts thereof, for use in the treatment and/or prevention of atopic dermatitis.

The combination according to the invention means in particular that said combined compounds are present within one and the same composition.

A subject of the invention is also the use of pyrrolidone-5-carboxylic acid in combination with at least one of the compounds chosen from citrulline, arginine and asparagine, in racemic form or in D- or L-isomer form, and/or salts thereof, in the manufacture of a medicament for use in the treatment and/or prevention of atopic dermatitis. A subject of the present invention is more particularly the use of pyrrolidone-5-carboxylic acid in combination with citrulline, or the use of pyrrolidone-5-carboxylic acid in combination with arginine, or the use of pyrrolidone-5-carboxylic acid in combination with asparagine, or the use of pyrrolidone-5-carboxylic acid in combination with citrulline and arginine, or the use of pyrrolidone-5-carboxylic acid in combination with citrulline and asparagine, or the use of pyrrolidone-5-carboxylic acid in combination with arginine and asparagine, or the use of pyrrolidone-5-carboxylic acid in combination with citrulline, arginine and asparagine, in racemic form or in D- or L-isomer form, and/or salts thereof.

The present invention also relates to a composition comprising, in a pharmaceutically acceptable carrier, pyrrolidone-5-carboxylic acid and at least one compound chosen from citrulline, arginine and asparagine, in racemic or isomer form, and/or salts thereof.

The composition according to the invention may be pharmaceutical, dermatological or cosmetic.

A subject of the present invention is also the use of the composition according to the invention in the preparation of a medicament for use in the prevention and/or treatment of atopic dermatitis (or eczema).

The term "physiologically acceptable carrier" is intended to mean a carrier compatible with human skin.

Pyrrolidone-5-carboxylic acid in L or D or D,L form corresponds to the following formula:

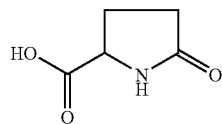

Citrulline in L or D or D,L form corresponds to the following formula:

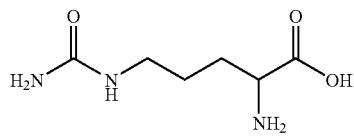 [SMILES: NC(=O)NCCCC(N)C(=O)O]

Arginine in L or D or D,L form corresponds to the following formula:

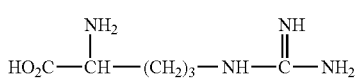

Asparagine in L or D or D,L for corresponds to the following formula:

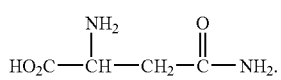

The term "isomer" is intended to mean in particular the D or L forms of pyrrolidone-5-carboxylic acid, of citrulline, of arginine or of asparagine. The term "racemic" is intended to mean a mixture of these D and L forms, also called D,L form.

The salts of the compounds according to the invention comprise salts with organic or inorganic bases, for example the alkali metal salts, such as the lithium salts, sodium salts, potassium salts; the alkaline-earth metal salts, such as the magnesium salts, calcium salts; the zinc salts; the salts of organic amines such as morpholine, piperazine.

The citrulline salts, arginine salts and asparagine salts can also be in the form of malates, chlorides, trifluoroacetates, hydrogen sulphates, sulphates and dihydrophosphates.

Preferably, the composition according to the invention, as defined above, comprises either pyrrolidone-5-carboxylic acid in combination with citrulline or pyrrolidone-5-carboxylic acid in combination with arginine or pyrrolidone-5-carboxylic acid in combination with asparagine, or pyrrolidone-5-carboxylic acid in combination with arginine and asparagine, or pyrrolidone-5-carboxylic acid in combination with citrulline and asparagine, or pyrrolidone-5-carboxylic acid in combination with citrulline and arginine, or pyrrolidone-5-carboxylic acid in combination with citrulline, arginine and asparagine, in racemic or isomer form, and/or a salt thereof.

The amount of pyrrolidone-5-carboxylic acid, of citrulline, of arginine or of asparagine in racemic or isomer form, or a salt thereof, that can be used in the compositions according to the invention depends, of course, on the desired effect and dosage, according to the patient to be treated and the method of administration, and can therefore vary to a large extent. In general, the pyrrolidone-5-carboxylic acid, the citrulline, the arginine and the asparagine will be present in an amount sufficient to obtain the desired hydration and a significant effect on the decrease in cutaneous manifestations of atopic dermatitis.

Preferably, the composition comprises an amount of each compound of between 0.001% and 15% by weight, preferably between 0.01% and 10% by weight, and more preferably between 0.5% and 5% by weight, relative to the total weight of the composition.

To give an order of magnitude:
the pyrrolidone-5-carboxylic acid in racemic or isomer form, or a salt thereof, when it is present in the composition, can represent from 0.001% to 15% (m/m), preferably from 0.01% to 10% (m/m), and more preferably from 0.5% to 5% (m/m) of the composition,
the citrulline in racemic or isomer form, or a salt thereof, when it is present in the composition, can represent from 0.001% to 15% (m/m), preferably from 0.01% to 10% (m/m), and more preferably from 0.5% to 5% (m/m) of the composition,
the arginine in racemic or isomer form, or a salt thereof, when it is present in the composition, can represent from 0.001% to 15% (m/m), preferably from 0.01% to 10% (m/m), and more preferably from 0.5% to 5% (m/m) of the composition,
the asparagine in racemic or isomer form, or a salt thereof, when it is present in the composition, can represent from 0.001% to 15% (m/m), preferably from 0.01% to 10% (m/m), and more preferably from 0.5% to 5% (m/m) of the composition.

These percentages are percentages by mass relative to the total mass of the composition (m/m).

The composition according to the invention is generally suitable for topical application to the skin and it therefore contains a physiologically acceptable medium, i.e. a medium that is compatible with the skin. The compositions according to the invention comprise a physiologically acceptable support or at least one pharmaceutically acceptable excipient, chosen according to the dermatological or pharmaceutical form desired.

The composition according to the invention is preferably in a form suitable for topical application to the skin. For example, it may be in the form of an optionally gelled, oily solution, an optionally two-phase dispersion of the lotion type, an emulsion obtained by dispersion of a fatty phase in an aqueous phase (O/W) or vice versa (W/O), or a triple emulsion (W/O/W or O/W/O) or a vesicular dispersion of ionic and/or non-ionic type. It may also be in the form of suspensions of microspheres or nanospheres or vesicles which may be lipid or polymeric or of hydrogels for controlled release. This topical composition may be in anhydrous form, in aqueous form or in the form of an emulsion. These compositions are prepared according to the usual methods. According to this invention, a composition in the form of an emulsion obtained by dispersion of a fatty phase in an aqueous phase (O/W) is preferably used.

This composition may be more or less fluid and may be in the form of salves, emulsions, creams, milks, ointments, impregnated pads, syndets, solutions, sera, gels, sprays or aerosols, foams, suspensions, lotions or sticks. The compositions in emulsion form are nevertheless preferred.

The pharmaceutical, preferably dermatological, compositions as described above may contain inert additives or even pharmacodynamically active additives, or combinations of these additives. In a known manner, the composition used according to the invention can therefore contain additives that are customary in the topical composition field, such as hydrophilic or lipophilic gelling agents, preserving agents such as para-hydroxybenzoic acid esters, additional moisturizing agents, calmatives, antioxidants, solvents, UV-A and UV-B screens, wetting agents, stabilizers; moisture regulators, pH regulators, osmotic pressure modifiers or emulsifiers.

The amounts of these various adjuvants are those conventionally used in the field under consideration, and for example from 0.01% to 20% of the total mass of the composition. Depending on their nature, these adjuvants may be introduced into the fatty phase, into the aqueous phase or into the vesicles. In any event, these adjuvants, and also the proportions thereof, will be chosen so as not to harm the desired properties of the moisturizing agents used according to the invention.

When the composition used according to the invention is an emulsion, the proportion of the fatty phase can range from 5% to 80% by weight, and preferably from 5% to 50% by weight, relative to the total weight of the composition. The oils, the emulsifiers and the coemulsifiers used in the composition in emulsion form are chosen from those conventionally used in the field under consideration. The emulsifier and the coemulsifier are present, in the composition, in a proportion ranging from 0.3% to 30% by weight, and preferably from 0.5% to 20% by weight, relative to the total weight of the composition.

As oils that can be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluorooils (perfluoropolyethers). Fatty alcohols (cetyl alcohol), fatty acids and waxes (carnauba wax, ozokerite) can also be used as fats.

As emulsifiers and coemulsifiers that can be used in the invention, mention may, for example, be made of fatty acid esters of polyethylene glycol, such as PEG 100 stearate, and fatty acid esters of glycerol, such as glyceryl stearate.

As hydrophilic gelling agents, mention may in particular be made of carboxyvinyl polymers (carbomer), acrylic copolymers such as acrylate/alkyl acrylate copolymers, polyacrylamides, polysaccharides, natural gums and clays, and as lipophilic gelling agents, mention may be made of modified clays such as bentones, metal salts of fatty acids, hydrophobic silica and polyethylenes.

As antioxidant, mention may be made of α-tocopherol, butylhydroxyanisole or butylhydroxytoluene, superoxide dismutase, ubiquinol or certain metal-chelating agents.

The term "additional moisturizing agent" is intended to mean:

either a compound that acts on the barrier function, with a view to maintaining the hydration of the stratum corneum, or an occlusive compound. Mention may be made of ceramides, sphingoid-based compounds, lecithins, glycosphingolipids, phospholipids, cholesterol and its derivatives, phytosterols (stigmasterol, beta-sitosterol, campesterol), fatty acids that are 12 to 20 carbons in length, essential fatty acids, 1,2-diacylglycerol, 4-chromanone, pentacyclic triterpenes such as ursolic acid, petroleum jelly and lanolin, glycerol, PEG 400, thiamorpholinone and its derivatives, and urea;

or a compound which directly increases the water content of the stratum corneum, such as threalose and its derivatives, hyaluronic acid and its derivatives, glycerol, pentanediol, sodium pidolate, xylitol, sodium lactate, glycerol polyacrylate, ectoin and its derivatives, chitosan, oligosaccharides, poly-saccharides or cyclic carbonates.

Among starting materials that are effective as calmatives, mention may be made, in a nonlimiting manner, of the following active agents: pentacyclic triterpenes, such as beta-glycyrrhetinic acid and its salts and/or its derivatives (glycyrrhetic acid monoglucuronide, stearyl glycyrrhetinate, 3-stearoyl-oxyglycyrrhetic acid), ursolic acid and its salts, oleanolic acid and its salts, betulinic acid and its salts; extracts of Paeonia suffruticosa and/or lactiflora, of *Rosmarinus officinalis*, of willow herb, of *Pygeum*, of *Boswellia serrata*, of *Centipeda cunnighami*, of *Helianthus annuus*, of *Cola nitida*, of clove and of *Bacopa moniera*; salicylic acid salts, and in particular zinc salicylate; algal extracts, in particular extracts of *Laminaria saccharina*; canola oil, tamanu oil, beauty-leaf oil, omega-3-unsaturated oils such as musk rose oil, black-currant oil, ecchium oil or fish oil; alpha-bisabolol and camomile extracts; allantoin; the phosphoric diester of vitamins E and C; capryloylglycine; tocotrienols; piperonal; aloe vera; phytosterols.

Mention may also be made of strontium salts; thermal springs, and in particular the thermal spring of the Vichy basin and the thermal spring of La Roche Posay; bacterial extracts, and in particular the extract of non-photosynthetic filamentous bacteria described in patent application EPO 761 204, preferably prepared from bacteria belonging to the Beggiatoales order, and more particularly to the genus *Vitreoscilla*. Preferably, a strain of *Vitreoscilla filiformis* is used according to the invention.

Mention may also be made of an extract of (preferably undifferentiated) cells of at least one plant of the family Iridaceae, obtained by in vitro culturing. The Iridacea plant preferably belongs to the *Iris* genus. In particular, it is preferred to use an aqueous extract of *Iris pallida*, as described in application EPO 765 668. Finally, mention may be made of an extract of at least one plant of the family Rosaceae, preferably cultivated in vivo. A plant belonging to the *Rosa* genus, advantageously of the species *Rosa gallica*, more preferably an aqueous-alcoholic extract of *Rosa gallica* petals, as described in patent application EPO 909 556, is preferably used according to the invention.

For a better understanding of the invention, its advantages, and specific objects attained by its use, reference should be had to the drawing and descriptive matter in which there are illustrated and described preferred embodiments of the invention.

Figure 2:
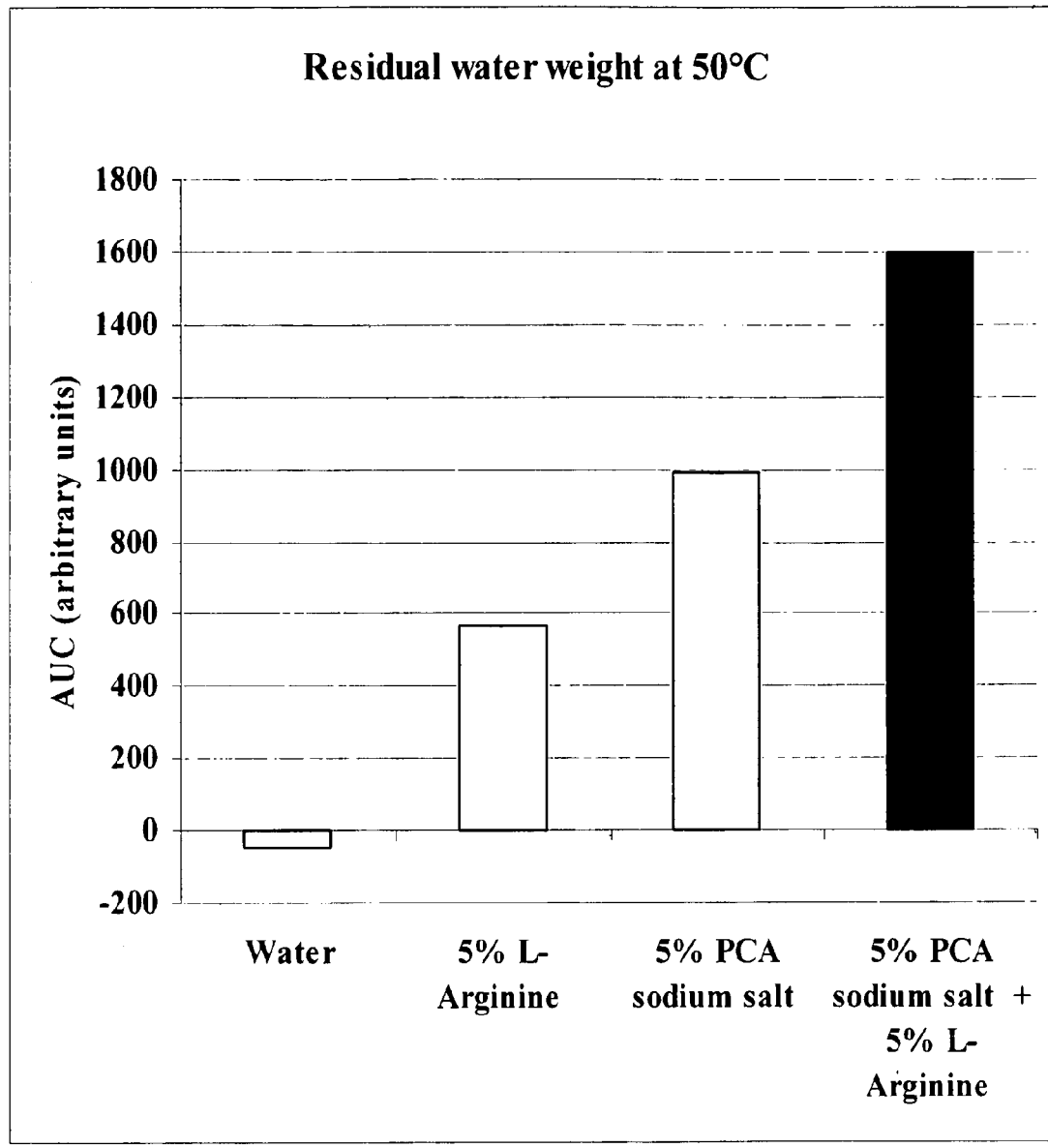

In the drawings:

FIG. 1 presents the variation of the residual water weight at 50° C. expressed as a percentage as a function of time for all 5% solutions versus water as negative control:

FIG. 2 presents the variation of the residual water at 50° C. expressed as area under the curve (AUC) measured from 45 to 120 minutes for all solutions.

Figure 3:
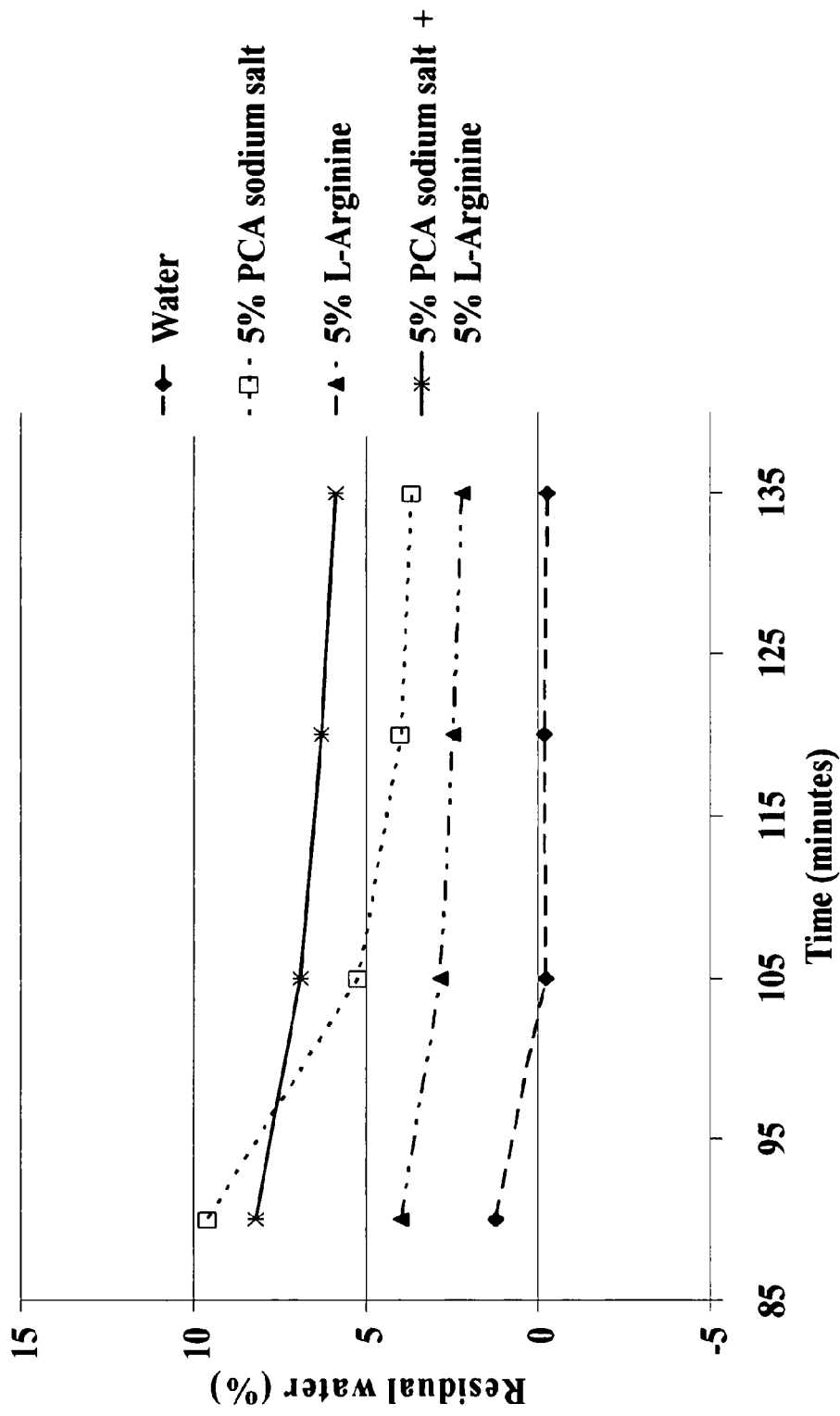
Figure 4:
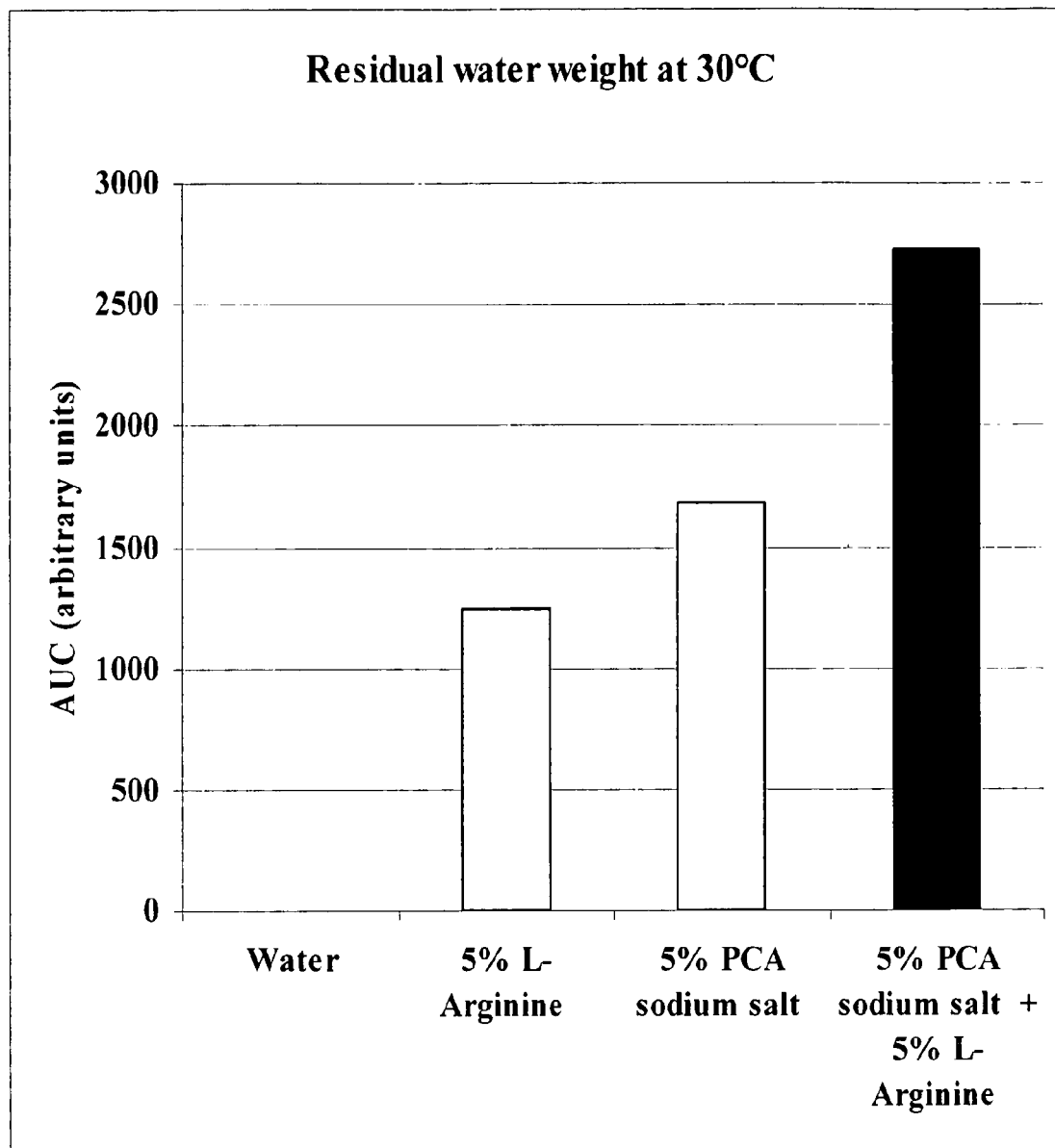

FIG. 3 presents the variation of the residual water weight at 30° C. expressed as a percentage as a function of time for all 5% solutions versus water as negative control:

FIG. 4 presents the variation of the residual water at 30° C. expressed as area under curve determined from 90 to 135 minutes for all solutions.

Figure 5:
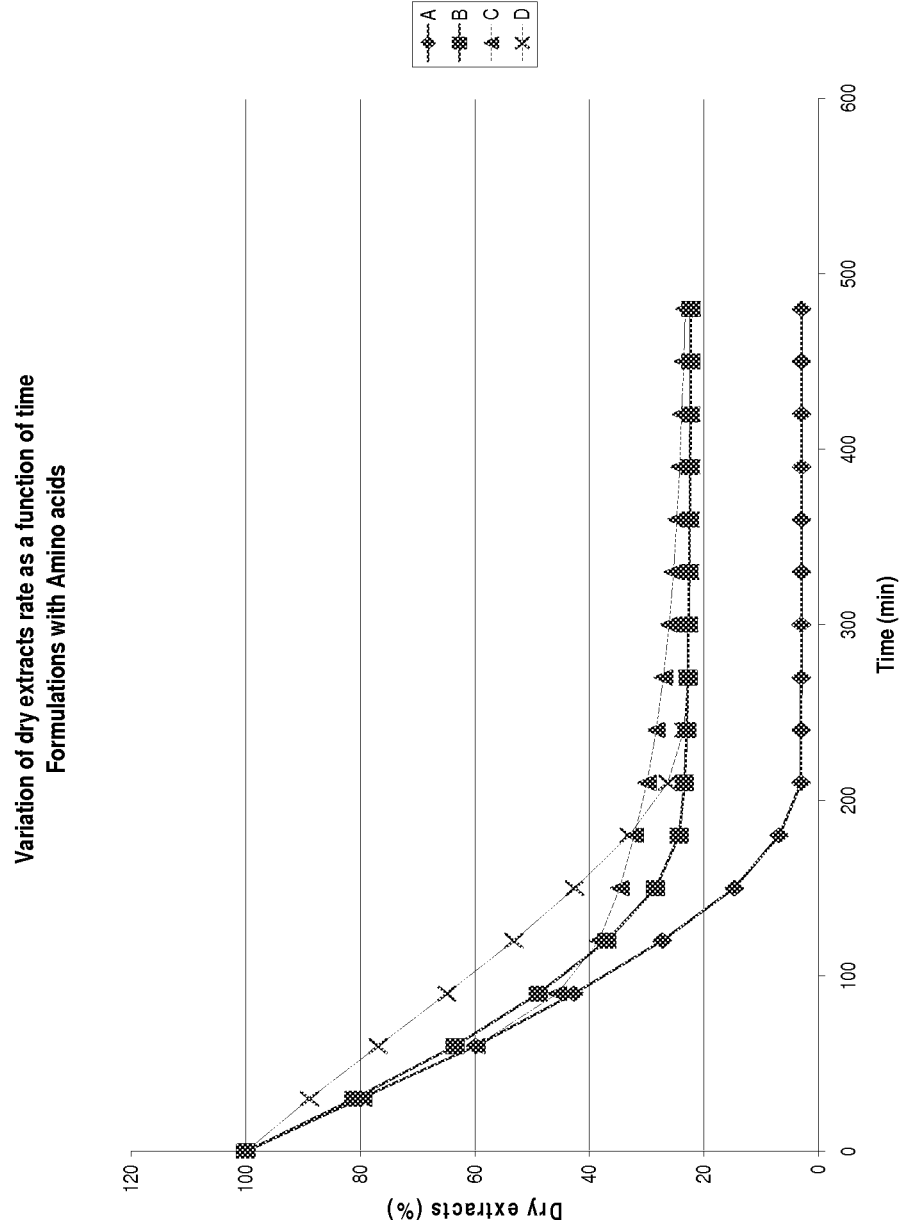

FIG. 5 presents the variation of the dry extracts rate as a function of time (min).

Figure 6:
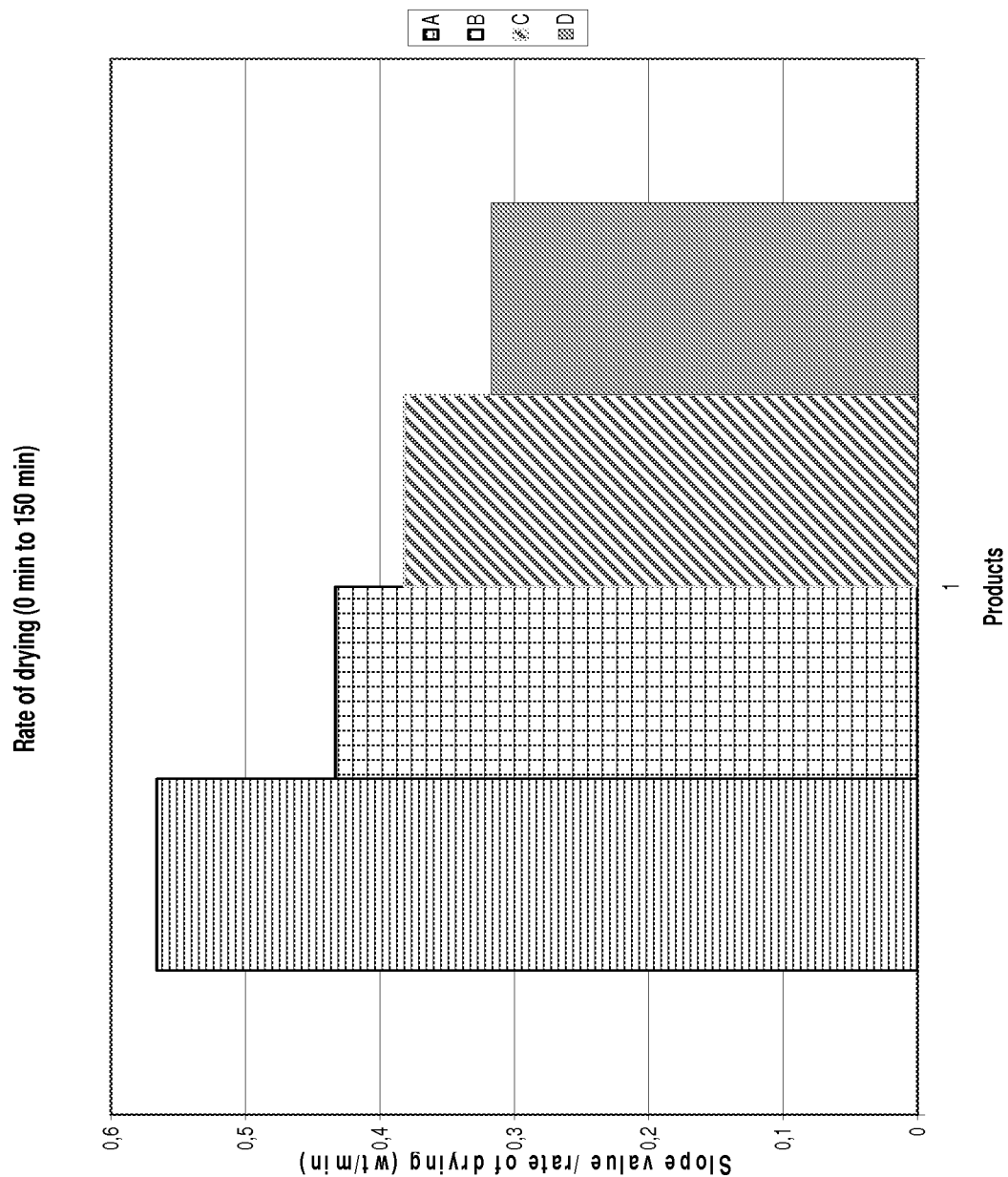

FIG. 6 presents the rate of drying/Slope value between 0 min and 150 min.

The following details studies that clearly demonstrate the benefit of composition used according to the invention.

The invention will also be illustrated by the following nonlimiting examples of composition. In these examples of composition, the amounts are indicated as percentage by weight.

I. Assessment of the Hygroscopic Properties of Amino Acids
Materials and Methods
Compounds:

2-Pyrrolidone-5-carboxylic acid sodium salt (PCA Na; CAS number 54571-67-4) was purchased from Solabia Cosmetics. L-Arginine [CAS number 74-79-3] was purchased from Sigma Aldrich.

Each compound was dissolved in water (w/w) to obtain a 5% solution. To prepare a 5% two-amino acid solution, the L-arginine powder was dissolved directly in the 5% PCA sodium salt solution (w/w).

Methods:

To assess the hygroscopic properties of amino acids, we studied the residual water weight of different solutions as a function of time. We determined the weight of residual water in each solution after different times in an atmosphere in which temperature and humidity were controlled in a thermal container (Vötsch VC0018). The temperature used for our assays was initially set at 50° C. and later at 30° C. to approximate skin conditions more closely. Humidity was set at 30%.

Using these parameters, we determined the weight of each solution before heating it and at different times during the heating. The heating lasted for 120 minutes at 50° C. and data was recorded from 45 to 120 minutes. At 30° C. the heating lasted for 135 minutes and data was recorded from 90 to 135 minutes. The residual weight expected at the end of the study which corresponds to the weight of the compound in the solution was calculated (for example, if the initial total weight for a 5% solution was 100 mg, the weight of the compound was 5 mg). The residual water weight of each solution was obtained by subtracting the expected weight of the compound from the total weight of the solution at different times. We considered the initial water weight to be 100%. In each experiment, water without any amino acids was used as negative control.

Results

We tested the hygroscopic properties of different solutions containing either PCA sodium salt alone, L-Arginine alone or the 2 amino acids. Each compound was used at 5%.

As a first experimental approach, we used conditions of forced evaporation at 50° C.

As can be seen in FIG. 1, the water, which didn't contain amino acid, evaporated totally after 45 minutes at 50° C. The addition of PCA Na or L-Arginine in water at 5% decreased the evaporation of the water contained in the solutions seen as an increase of the percentage of residual water weight after 120 minutes at 50° C. This increase was higher when the amino acids were used in combination.

As can be seen in FIG. 2, the residual water weight observed when the amino acids were used in combination at 5% was higher as those observed when the amino acids were used alone at 5%.

Based on the positive results with forced evaporation at 50° C., we next turned our attention to experimental conditions that more closely reflect physiological conditions, and performed the evaporation studies at 30° C. (The temperature of the skin surface is around 30-32° C.)

As can be seen from FIGS. 3 and 4, results similar to those observed at 50° C. were obtained at 30° C.

To summarize, all of these results confirmed the hygroscopic properties of the 2 amino acids throughout the study of the residual water weight. We observed that the combination of the two amino acids have better hygroscopic properties than either amino acid when used alone.

II. Thermogravimetry Analysis
1. Aim of the Study

A test, namely Thermogravimetry analysis, is carried out on different formulations in order to assess the hygroscopic properties of amino acids and cutaneous hydration. For this, the rate of water loss as a function of time is studied at 32° C. to reproduce the conditions of application of the formulation on the skin (temperature of the skin).

2. Materials and Methods

Sartorius MA100 analyzer is used to determine humidity content of liquid, solid and semi-solid substances with thermogravimetry principle.

This process permits to determine a weight loss due to heating. The formula is weighed before and after heating in order to measure the weight loss.

Operating Conditions

The table hereafter describes the operating conditions of the test (cf table 1):

TABLE 1

| Operating conditions TEST | |
|---|---|
| Parameters | Value of the parameter |
| Heat program | Standard desiccation |
| Final temperature | 32° C. |
| Beginning of the analysis | With stability |
| End of the analysis | 480 min |
| Results | Dry extracts (%) |

These operating conditions have been chosen in order to mimic skin conditions (The temperature of the skin is around 30-32° C.)

3. Results and Discussions 3.1. Tested Products

All tested products are based on a formulation containing the gelling agent Natrosol 250HHX (INCI name Hydroxyethylcellulose) at 0.5%. The pH of the products is comprised between 5.0 and 5.5 (adjusted by citric acid and sodium citrate). Table 2 below presents qualitative and quantitative composition of the tested products:

TABLE 2

Formulations presentation

Excipients (%)

| Trade name | INCI name | A | B | C | D |
|---|---|---|---|---|---|
| Natrosol 250HHX | Hydroxyethylcellulose | 0.5 | 0.5 | 0.5 | 0.5 |
| Citric acid/sodium citrate USP 2H20 | Citric acid/sodium citrate | | pH 5.5 +/− 0.5 | | |
| Nalidone | PCA Na (sodium pyrrolidone carboxylic acid) | — | 4.0 | 4.0 | 4.0 |
| L-Citrulline | Citrullin | — | — | 12.0 | — |
| L-Arginine | Arginin | — | 12.0 | — | — |
| L-Asparagine | Asparagin | — | — | — | 12.0 |
| Purified water | Aqua | 97.1 | 81.1 | 81.1 | 81.1 |

3.2 Thermogravimetry Analysis: Results

Thermogravimetry analysis, demonstrates a steep fall of the dry extracts rate between 0 and around 150 minutes, indicating that evaporation occurs very quickly. Thereafter, stable evaporation is observed between 150 and 480 min.

The evaporation rate at the end of the analysis is less important when there are amino acids in the product.

To further quantify the hygroscopic properties of amino acids, the slope/gradient between 0 and 150 min was calculated (cf FIG. 6). The lower the slope/gradient for a product the better are its hygroscopic properties.

The highest drying rate is observed for product A (without amino acids). This means that product A does not retain evaporation of water unlike products which contain amino acids. Addition of amino acids reduces the rate of water loss, as observed by the lower rate of drying of products B, C, and D which contain amino acid.

4. Conclusion

To summarize, thermogravimetry analysis demonstrated that the rate of evaporation is lower for products which contain amino acids.

Amino acids are able to reduce the rate of water loss.

The results described in sections I and II, allowed us to document that amino acids are hygroscopic agents and, particularly if combined, can play a significant role in cutaneous hydration.

III. Examples of Compositions

1) Oil-In-Water Emulsion

| Ingredients | Concentration % |
|---|---|
| Water | Qs 100 |
| Glycerol | 5 |
| Carbomer | 0.1 |
| Cetyl alcohol | 1 |
| Stearyl alcohol | 1 |
| Glyceryl stearate/PEG 100 glyceryl stearate | 3 |
| Isopropyl palmitate | 10 |
| Citrulline | 3 |
| Sodium pyrrolidone-5-carboxylate | 1 |
| EDTA | 0.1 |
| Cyclomethicone 5 | 1 |
| pH adjuster | Qs pH 6 |
| Preserving agent | 0.3 |
| Water | Qs 100 |
| Glycerol | 5 |
| Carbomer | 0.1 |
| Cetyl alcohol | 1 |
| Stearyl alcohol | 1 |
| Glyceryl stearate/PEG 100 glyceryl stearate | 3 |
| Isopropyl palmitate | 10 |
| Arginine | 3 |
| Sodium pyrrolidone-5-carboxylate | 1 |
| EDTA | 0.1 |
| Cyclomethicone 5 | 1 |
| pH adjuster | Qs pH 6 |
| Preserving agent | 0.3 |

2) Oil-In-Water Lipocream

| Ingredients | Concentration % |
|---|---|
| Water | Qs 100 |
| Xanthan gum | 0.2 |
| Magnesium aluminium silicate | 0.8 |
| Glyceryl monostearate | 6.25 |
| Ceteareth 20 | 3.75 |
| Mineral oil | 15 |
| Liquid petroleum jelly | 11 |
| Isopropyl palmitate | 13 |
| Stearyl alcohol | 1 |
| EDTA | 0.1 |
| Sodium pyrrolidone-5-carboxylate | 1.5 |
| Citrulline | 3 |
| Arginine | 1.5 |
| pH adjuster | Qs pH 6 |
| Water | Qs 100 |
| Xanthan gum | 0.2 |
| Magnesium aluminium silicate | 0.8 |
| Glyceryl monostearate | 6.25 |
| Ceteareth 20 | 3.75 |
| Mineral oil | 15 |
| Liquid petroleum jelly | 11 |
| Isopropyl palmitate | 13 |
| Stearyl alcohol | 1 |
| EDTA | 0.1 |
| Sodium pyrrolidone-5-carboxylate | 3 |
| Asparagine | 3 |
| pH adjuster | Qs pH 6 |

3) Gel

| Ingredients | Concentration % |
|---|---|
| Water | QS 100 |
| Carboxymethylcellulose | 1.25 |
| Glycerol | 5 |
| Preserving agent | 0.3 |
| EDTA | 0.1 |
| Sodium pyrrolidone-5-carboxylate | 2 |
| Arginine | 3 |
| Citrulline | 2 |
| Asparagine | 2 |

4) Cream-Gel

| Ingredients | Concentration % |
|---|---|
| Water | QS 100 |
| Glycerol | 5 |
| Carbomer | 0.15 |
| Acrylates/C10-30 alky acrylate crosspolymer (Pemulen TR1) | 0.3 |
| Polysorbate 80 | 1 |
| EDTA | 0.1 |

-continued

| Ingredients | Concentration % |
|---|---|
| Propylene glycol | 3 |
| Preserving agent | 0.3 |
| Sodium pyrrolidone-5-carboxylate | 1 |
| Asparagine | 2 |
| Citrulline | 2 |

The invention claimed is:

1. A dermatologic composition for treating atopic dermatitis comprising:
   at least one first entity chosen from pyrrolidone-5-carboxylic acid, isomers thereof, racemates thereof, and salts of pyrrolidone-5-carboxylic acid, isomers thereof, racemates thereof, and
   at least one second entity chosen from citrulline, arginine, asparagine, isomers thereof, racemates thereof, and salts of citrulline, arginine, asparagine, isomers thereof, racemates thereof;
   wherein:
   the at least one first entity and the at least one second entity are each present in an amount ranging from 0.5% to 15% by weight of the dermatologic composition;
   and wherein said dermatologic composition for treating atopic dermatitis further comprises a physiologically acceptable carrier.

2. The dermatologic composition according to claim 1, wherein said at least one second entity is chosen from citrulline, isomers thereof, racemates thereof, and salts of citrulline, isomers thereof, racemates thereof.

3. The dermatologic composition according to claim 1, wherein said at least one second entity is chosen from arginine, isomers thereof, racemates thereof, and salts of arginine, isomers thereof, racemates thereof.

4. The dermatologic composition according to claim 1, wherein said at least one second entity is chosen from asparagine, isomers thereof, racemates thereof, and salts of asparagine, isomers thereof, racemates thereof.

5. The dermatologic composition according to claim 1, wherein said at least one second entity is a combination of at least one entity chosen from citrulline, isomers thereof, racemates thereof, and salts of citrulline, isomers thereof, racemates thereof, and at least one entity chosen from arginine, isomers thereof, racemates thereof, and salts of arginine, isomers thereof, racemates thereof.

6. The dermatologic composition according to claim 1, wherein said at least one second entity is a combination of at least one entity chosen from citrulline, isomers thereof, racemates thereof, and salts of citrulline, isomers thereof, racemates thereof, and at least one entity chosen from asparagine, isomers thereof, racemates thereof, and salts of asparagine, isomers thereof, racemates thereof.

7. The composition according to claim 1, wherein said at least one second entity is a combination of at least one entity chosen from arginine, isomers thereof, racemates thereof, and salts of arginine, isomers thereof, racemates thereof, and at least one entity chosen from asparagine, isomers thereof, racemates thereof, and salts of asparagine, isomers thereof, racemates thereof.

8. The dermatologic composition according to claim 1, wherein the at least one first entity and the at least one second entity are independently each present in an amount ranging from 0.5% to 10% by weight, relative to the total weight of the dermatologic composition.

9. The dermatologic composition according to claim 1, wherein the at least one first entity and the at least one second entity are independently each present in an amount ranging from 0.5% to 5% by weight, relative to the total weight of the dermatologic composition.

10. The dermatologic composition according to claim 1, wherein the dermatologic composition is in a form suitable for topical application.

11. The dermatologic composition according to claim 10 wherein the dermatologic composition is in a form chosen from salves, emulsions, creams, milks, ointments, impregnated pads, syndets, solutions, sera, gels, sprays or aerosols, foams, suspensions, lotions, washes, and sticks.

12. A method for treating atopic dermatitis comprising administering, to a subject in need thereof, a combination comprising:
   at least one first entity chosen from pyrrolidone-5-carboxylic acid, isomers thereof, racemates thereof, and salts of pyrrolidone-5-carboxylic acid, isomers thereof, racemates thereof, and
   at least one second entity chosen from citrulline, arginine, asparagine, isomers thereof, racemates thereof, and salts of citrulline, arginine, asparagine, isomers thereof, racemates thereof;
   wherein:
   the at least one first entity and the at least one second entity are each present in an amount ranging from 0.5% to 15% by weight of the dermatologic composition.

13. A method for treating atopic dermatitis comprising administering, to a subject in need thereof, a dermatologic composition comprising a physiologically acceptable carrier and:
   at least one first entity chosen from pyrrolidone-5-carboxylic acid, isomers thereof, racemates thereof, and salts of pyrrolidone-5-carboxylic acid, isomers thereof, racemates thereof, and
   at least one second entity chosen from citrulline, arginine, asparagine, isomers thereof, racemates thereof, and salts of citrulline, arginine, asparagine, isomers thereof, racemates thereof;
   wherein:
   the at least one first entity and the at least one second entity are each present in an amount ranging from 0.5% to 15% by weight of the dermatologic composition.

14. The method according to claim 12, wherein the combination is administered topically and/or applied to skin.

15. The method according to claim 13, wherein the dermatologic composition is administered topically and/or applied to skin.

16. The dermatologic composition according to claim 1, further comprising at least one additive chosen from hydrophilic or lipophilic gelling agents, preserving agents, moisturizing agents, calmatives, antioxidants, solvents, UVA and UVB screens, wetting agents, stabilizers, moisture regulators, pH regulators, osmotic pressure modifiers, and emulsifiers.

17. The dermatologic composition according to claim 16, wherein the at least one additive is present in an amount ranging from 0.01% to 20%, relative to the total mass of the dermatologic composition.

* * * * *